United States Patent
Lee et al.

(10) Patent No.: US 10,059,149 B2
(45) Date of Patent: Aug. 28, 2018

(54) ORGANOLITHIUM COMPOUND, METHOD FOR PREPARING MODIFIED CONJUGATED DIENE-BASED POLYMER USING THE SAME, AND MODIFIED CONJUGATED DIENE-BASED POLYMER

(71) Applicant: LG Chem, Ltd., Seoul (KR)

(72) Inventors: Ho Young Lee, Daejeon (KR); No Ma Kim, Daejeon (KR); Min Sik Mun, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 15/555,729

(22) PCT Filed: Nov. 2, 2016

(86) PCT No.: PCT/KR2016/012537
§ 371 (c)(1),
(2) Date: Sep. 5, 2017

(87) PCT Pub. No.: WO2017/078408
PCT Pub. Date: May 11, 2017

(65) Prior Publication Data
US 2018/0056716 A1   Mar. 1, 2018

(30) Foreign Application Priority Data
Nov. 2, 2015   (KR) .................. 10-2015-0153294

(51) Int. Cl.
| | |
|---|---|
| B60C 1/00 | (2006.01) |
| C08F 212/08 | (2006.01) |
| C08F 210/18 | (2006.01) |
| C08K 5/56 | (2006.01) |
| C08L 9/06 | (2006.01) |
| C08F 2/04 | (2006.01) |
| C07C 211/09 | (2006.01) |
| C07F 1/02 | (2006.01) |

(52) U.S. Cl.
CPC .................. B60C 1/00 (2013.01); C08F 2/04 (2013.01); C08F 210/18 (2013.01); C08F 212/08 (2013.01); C08K 5/56 (2013.01); C08L 9/06 (2013.01); C07C 211/09 (2013.01); C07F 1/02 (2013.01); C08F 2500/21 (2013.01)

(58) Field of Classification Search
CPC .. B60C 1/00; C08F 2/04; C08F 212/08; C08F 210/18; C08F 2500/21; C08L 9/06; C08K 5/56; C07F 1/02; C07C 211/09
See application file for complete search history.

(56) References Cited

U.S. PATENT DOCUMENTS

| | | |
|---|---|---|
| 5,354,822 A | 10/1994 | Antkowiak et al. |
| 9,109,073 B1 | 8/2015 | Ma et al. |
| 2002/0035294 A1 | 3/2002 | Halasa et al. |
| 2008/0033110 A1 | 2/2008 | Suzuki et al. |
| 2012/0101212 A1* | 4/2012 | Yoon ................ C07F 1/02 524/534 |
| 2012/0259056 A1 | 10/2012 | Suzuki et al. |
| 2014/0152845 A1 | 6/2014 | Seger et al. |
| 2014/0309390 A1 | 10/2014 | Yan |
| 2015/0099852 A1 | 4/2015 | Lawson et al. |
| 2016/0159957 A1 | 6/2016 | Choi et al. |

FOREIGN PATENT DOCUMENTS

| | | |
|---|---|---|
| EP | 0709408 A1 | 5/1996 |
| EP | 2060604 A1 | 5/2009 |
| KR | 20040070047 A | 8/2004 |
| KR | 20150056484 A | 5/2015 |
| WO | 2005097845 A1 | 10/2005 |
| WO | 2013090885 A2 | 6/2013 |

OTHER PUBLICATIONS

Search report from International Application No. PCT/KR2016/012537, dated Jan. 31, 2017.
Peterson, Donald J., et al., "Functionally-Substituted N,N-Dialkylaminomethyllithium Compounds." Journal of Organometallic Chemistry, vol. 66, 1974, pp. 209-217.
Extended European Search Report for Application No. EP16862424 dated Jan. 30, 2018.

* cited by examiner

*Primary Examiner* — Alexander Kollias
(74) *Attorney, Agent, or Firm* — Lerner, David, Littenberg, Krumholz & Mentlik, LLP

(57) ABSTRACT

The present invention relates to an organolithium compound, and a method for preparing a modified conjugated diene-based polymer using the same. A modified conjugated diene-based polymer having good compatibility with an inorganic filler and improved processability may be provided, and by using a rubber composition including such modified conjugated diene-based polymer, a tire having excellent exothermic properties, tensile strength, abrasion resistance, low fuel consumption and wet traction, and low rolling resistance may be provided.

12 Claims, No Drawings

ORGANOLITHIUM COMPOUND, METHOD FOR PREPARING MODIFIED CONJUGATED DIENE-BASED POLYMER USING THE SAME, AND MODIFIED CONJUGATED DIENE-BASED POLYMER

CROSS-REFERENCE TO RELATED APPLICATIONS

This application is a national phase entry under 35 U.S.C. § 371 of International Application No. PCT/KR2016/012537, filed Nov. 2, 2016, which claims priority to Korean Patent Application No. 10-2015-0153294, filed Nov. 2, 2015, the disclosures of which are incorporated herein by reference.

TECHNICAL FIELD

The present invention relates to an organolithium compound, a method for preparing a modified conjugated diene-based polymer using the same, and a modified conjugated diene-based polymer.

BACKGROUND ART

With respect to the latest trends in the automobile industry, durability and lowering fuel consumption are constant requirements, and efforts to satisfy such requirements are continuously underway. In particular, many attempts have been made at reinforcing the physical properties of rubber which is a material for automobile tires, specifically, tire treads which make direct contact with the ground. While tire treads conventionally used an inorganic filler, etc. in combination with a conjugated diene-based rubber to reinforce the above-described physical properties, defects such as a large hysteresis loss or reduced dispersibility occurred.

Accordingly, as a tire tread material for improving the performance of automobile tires, the development of rubbers having good processability, excellent wet traction and mechanical strength, and low rolling resistance is required.

To this end, while research on a method of preparing a modified conjugated diene-based polymer has been done in, for example, WO2005-097845 A1, the effects thereof are insufficient.

DISCLOSURE OF THE INVENTION

Technical Problem

The present invention has been devised in consideration of the above-mentioned problems, and the object of the present invention is to provide an organolithium compound having a novel structure.

Another object of the present invention is to provide a modified conjugated diene-based polymer including a functional group derived from the organolithium compound.

Still another object of the present invention is to provide a method for preparing a modified conjugated diene-based polymer using the organolithium compound as a polymerization initiator.

In addition, still another object of the present invention is to provide a modified conjugated diene-based polymer rubber composition including the modified conjugated diene-based polymer. Further another object of the present invention is to provide a tire including the rubber composition.

Technical Solution

To solve the above-described tasks, the present invention provides an organolithium compound represented by the following Formula 1:

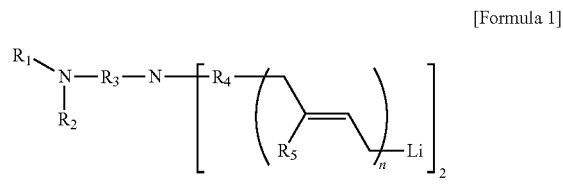

[Formula 1]

In Formula 1, $R_1$, $R_2$ and $R_5$ are each independently a monovalent hydrocarbon group having 1 to 10 carbon atoms, $R_3$ and $R_4$ are each independently a divalent hydrocarbon group having 1 to 10 carbon atoms, and n is an integer of 1 to 5.

In addition, there is provided in the present invention a modified conjugated diene-based polymer represented by the following Formula 3:

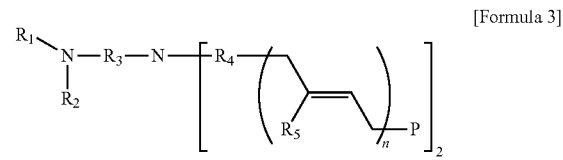

[Formula 3]

In Formula 3, $R_1$, $R_2$ and $R_5$ are each independently a monovalent hydrocarbon group having 1 to 10 carbon atoms, $R_3$ and $R_4$ are each independently a divalent hydrocarbon group having 1 to 10 carbon atoms, n is an integer of 1 to 5, and P is a conjugated diene-based polymer chain.

In addition, the present invention provides a method for preparing a modified conjugated diene-based polymer, comprising polymerizing conjugated diene-based monomers, or conjugated diene-based monomers and aromatic vinyl-based monomers in the presence of an organolithium compound represented by Formula 1 in a hydrocarbon solvent.

In addition, the present invention provides a rubber composition including the modified conjugated diene-based polymer, and a tire including the rubber composition.

Advantageous Effects

The organolithium compound represented by Formula 1 according to the present invention is used as a polymerization initiator of a conjugated diene-based polymer, and may provide the polymer chain of the conjugated diene-based polymer with a functional group.

Since the polymer chain in the modified conjugated diene-based polymer according to the present invention is combined with a functional group derived from the organolithium compound represented by Formula 1, affinity with a filler, specifically with a silica-based filler may be excellent.

In addition, according to the preparation method of the present invention, a modified conjugated diene-based polymer may be easily prepared by using the organolithium compound represented by Formula 1.

Also, since the rubber composition according to the present invention includes a modified conjugated diene-based polymer having excellent affinity with a filler, the processability thereof may be good, and as a result, molded articles, for example, tires manufactured using the rubber composition may have excellent tensile strength, abrasion resistance, low fuel consumption ratio and wet traction, and low rolling resistance.

BEST MODE FOR CARRYING OUT THE INVENTION

Hereinafter, the present invention will now be described in more detail in order to assist the understanding of the present invention.

It will be understood that words or terms used in the specification and claims shall not be interpreted as the meaning defined in commonly used dictionaries. It will be further understood that the words or terms should be interpreted as having a meaning that is consistent with their meaning of the technical idea of the invention, based on the principle that an inventor may properly define the meaning of the words or terms to best explain the invention.

The present invention provides an organolithium compound having a novel structure, which may be used as a polymerization initiator during the preparing of a polymer including conjugated diene-based monomer-derived units.

The organolithium compound according to an embodiment of the present invention is characterized in being represented by the following Formula 1:

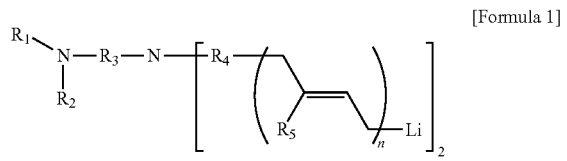

[Formula 1]

In Formula 1, $R_1$, $R_2$ and $R_5$ are each independently a monovalent hydrocarbon group having 1 to 10 carbon atoms, $R_3$ and $R_4$ are each independently a divalent hydrocarbon group having 1 to 10 carbon atoms, and n is an integer of 1 to 5.

In Formula 1, $R_1$, $R_2$ and $R_5$ are each independently a monovalent hydrocarbon group having 1 to 10 carbon atoms, and particularly, $R_1$, $R_2$ and $R_5$ may be each independently selected from the group consisting of an alkyl group having 1 to 10 carbon atoms, a cycloalkyl group having 3 to 10 carbon atoms, and an arylalkyl group having 6 to 10 carbon atoms.

In addition, in Formula 1, $R_3$ and $R_4$ are each independently a divalent hydrocarbon group having 1 to 10 carbon atoms, and particularly, may be an alkylene group having 1 to 10 carbon atoms such as methylene, ethylene and propylene; or an arylene group having 6 to 10 carbon atoms such as phenylene.

In particular, the organolithium compound may be Formula 1 where $R_1$, $R_2$ and $R_5$ are each independently an alkyl group having 1 to 6 carbon atoms, $R_3$ and $R_4$ are each independently an alkylene group having 1 to 6 carbon atoms, and n is an integer of 1 to 3. More particularly, Formula 1 may be represented by the following Formula 2:

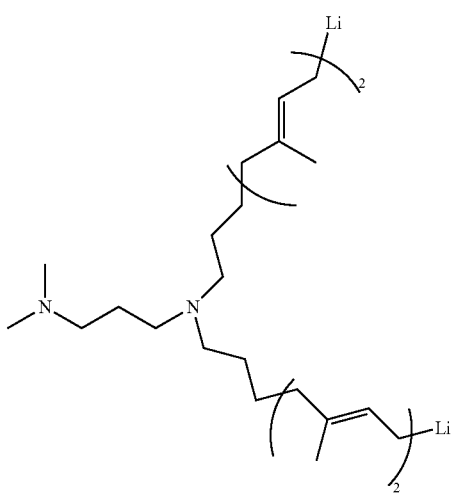

[Formula 2]

The organolithium compound according to an embodiment of the present invention may be used as a polymerization initiator of a polymer. Particularly, the organolithium compound may be used as a polymerization initiator during the preparing of a polymer to introduce a functional group into a polymer chain, thereby playing the role of modifying the structure, characteristics and physical properties of the polymer. In this case, the polymer may be a polymer including conjugated diene-based monomer-derived units. That is, the organolithium compound may be a polymerization initiator for a polymer including conjugated diene-based monomer-derived units.

In addition, there is provided in the present invention a modified conjugated diene-based polymer represented by the following Formula 3:

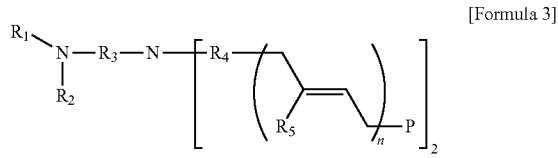

[Formula 3]

In Formula 3, $R_1$, $R_2$ and $R_5$ are each independently a monovalent hydrocarbon group having 1 to 10 carbon atoms, $R_3$ and $R_4$ are each independently a divalent hydrocarbon group having 1 to 10 carbon atoms, n is an integer of 1 to 5, and P is a conjugated diene-based polymer chain.

The modified conjugated diene-based polymer according to an embodiment of the present invention may be prepared by the following preparation method using the organolithium compound represented by the above Formula 1. By including the functional group derived from the organolithium compound represented by the above Formula 1, the physical properties of the polymer may be improved.

In particular, the modified conjugated diene-based polymer represented by the above Formula 3 may include an amine group derived from the organolithium compound represented by the above Formula 1, and thus may have good affinity with a filler such as silica. As a result, the abrasion resistance, low fuel consumption properties and processability of a rubber composition including the modified conjugated diene-based polymer and a molded article such as a tire manufactured from the rubber composition may be improved.

In particular, the modified conjugated diene-based polymer represented by the above Formula 3 may be represented by the following Formula 4:

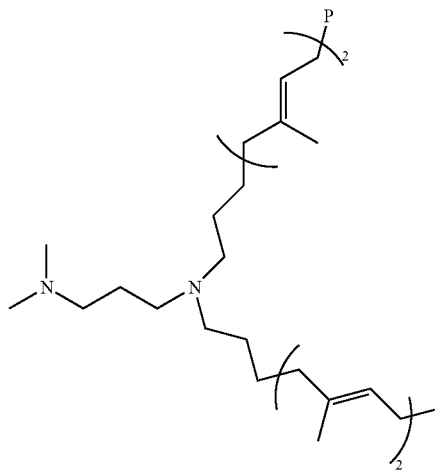

[Formula 4]

In Formula 4, P is a conjugated diene-based polymer chain.

Meanwhile, the modified conjugated diene-based polymer according to an embodiment of the present invention may be a homopolymer or a copolymer and may be prepared by the following preparation method.

In particular, when the modified conjugated diene-based polymer is a homopolymer, the polymer may be a homopolymer of conjugated diene-based monomers, and P in Formula 3 may be a polymer chain derived from conjugated diene-based monomers. In addition, when the modified conjugated diene-based polymer is a copolymer, the polymer may include conjugated diene-based monomer-derived units and aromatic vinyl-based monomer-derived units, and P in Formula 3 may be a copolymer chain derived from the conjugated diene-based monomers and the aromatic vinyl-based monomers. In addition, when the modified conjugated diene-based polymer is a copolymer, the copolymer may be a random copolymer. In this case, the conjugated diene-based copolymer chain may be a polymer chain obtained by including from 0.0001 parts by weight to 50 parts by weight, particularly, from 10 parts by weight to 40 parts by weight, or from 15 parts by weight to parts by weight of the aromatic vinyl-based monomer-derived units on the basis of 100 parts by weight of the total amount of the conjugated diene-based monomer-derived units and the aromatic vinyl-based monomer-derived units.

Here, the "random copolymer" may mean randomly arranged constituting units of a copolymer.

In addition, the modified conjugated diene-based polymer may have a molecular weight distribution (Mw/Mn) of 0.5 to 10, particularly, 0.5 to 5, more particularly 1 to 5. When the molecular weight distribution of the modified conjugated diene-based polymer satisfies the above range, mixing characteristics with inorganic particles may be excellent, and the physical properties of the polymer may be improved and the processability thereof may be largely improved.

In addition, the modified conjugated diene-based polymer may have the vinyl content of 5 wt % or more, particularly, from 8 wt % to 70 wt %.

The vinyl content means an amount of units having vinyl groups, or an amount of not 1,4-added but 1,2-added modified conjugated diene-based monomers on the basis of 100 wt % of conjugated diene-based monomers.

When the vinyl content of the modified conjugated diene-based polymer satisfies the above range, the glass transition temperature of a polymer increases, and when applying the polymer to a tire, physical properties required for the tire such as driving resistance and braking force may be satisfied, and fuel consumption decreasing effect may be attained.

In addition, there is provided in the present invention a method for preparing a modified conjugated diene-based polymer using the organolithium compound represented by Formula 1 below.

A preparation method according to an embodiment of the present invention comprises a step of polymerizing conjugated diene-based monomers, or conjugated diene-based monomers and aromatic vinyl-based monomers in the presence of an organolithium compound represented by the following Formula 1 in a hydrocarbon solvent (step A):

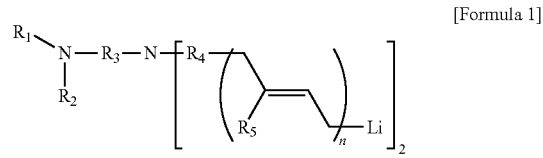

[Formula 1]

In Formula 1, $R_1$, $R_2$ and $R_5$ are each independently a monovalent hydrocarbon group having 1 to 10 carbon atoms, $R_3$ and $R_4$ are each independently a divalent hydrocarbon group having 1 to 10 carbon atoms, and n is an integer of 1 to 5.

Particular examples of the organolithium compound represented by Formula 1 may be the same as described above.

Step A is a step for preparing an active polymer in which a functional group derived from the organolithium compound represented by the above Formula 1 is combined with at least one terminal thereof, and is performed by polymerizing conjugated diene-based monomers, or conjugated diene-based monomers and aromatic vinyl-based monomers in the presence of the organolithium compound represented by the above Formula 1 in a hydrocarbon solvent.

In the polymerization of step A, a single type of conjugated diene-based monomers, or both types of conjugated diene-based monomers and aromatic vinyl-based monomers may be used as monomers. That is, the polymer prepared through the preparation method according to an embodiment of the present invention may be a conjugated diene-based monomer homopolymer, or a copolymer derived from conjugated diene-based monomers and aromatic vinyl-based monomers.

The conjugated diene-based monomer may be, without specific limitation, at least one selected from the group consisting of, for example, 1,3-butadiene, 2,3-dimethyl-1,3-butadiene, piperylene, 3-butyl-1,3-octadiene, isoprene, and 2-phenyl-1,3-butadiene.

In the case where both the conjugated diene-based monomers and the aromatic vinyl-based monomers are used as the monomers, the conjugated diene-based monomers may be used in an amount such that an amount of the conjugated diene-based monomer-derived units in a finally prepared modified conjugated diene-based polymer is 60 wt % or more, particularly, from 60 wt % to 90 wt %, more particularly, from 60 wt % to 85 wt %.

The aromatic vinyl-based monomer may be, without specific limitation, at least one selected from the group consisting of, for example, styrene, α-methylstyrene, 3-methylstyrene, 4-methylstyrene, 4-propylstyrene, 1-vinylnaphthalene, 4-cyclohexylstyrene, 4-(p-methylphenyl)styrene, and 1-vinyl-5-hexylnaphthalene.

In the case where both the conjugated diene-based monomers and the aromatic vinyl-based monomers are used together as the monomers, the aromatic vinyl-based monomers may be used in an amount such that an amount of the aromatic vinyl-based monomer-derived units in a finally prepared modified conjugated diene-based polymer is 40 wt % or less, particularly, from 10 wt % to 40 wt %, more particularly, from 15 wt % to 40 wt %.

The hydrocarbon solvent is not specifically limited and may be at least one selected from the group consisting of, for example, n-pentane, n-hexane, n-heptane, isooctane, cyclohexane, toluene, benzene and xylene.

The organolithium compound may be used from 0.01 mmol to 10 mmol, from 0.05 mmol to 5 mmol, from 0.1 mmol to 2 mmol, or from 0.1 mmol to 1 mmol on the basis of 100 g of total monomers. If the amount of the organolithium compound satisfies the above range, an optimized conjugated diene-based polymer for preparing a modified conjugated diene-based polymer may be obtained.

The polymerization of step A may be performed by further adding a polar additive as needed, and the polar additive may be added in an amount of 0.001 g to 50 g, 0.01 g to 10 g, 0.005 g to 1 g, or 0.005 g to 0.2 g on the basis of 100 g of total monomers.

In addition, the amount of the polar additive may be from 0.001 g to 10 g, from 0.005 g to 1 g, or from 0.005 g to 0.2 g on the basis of 1 mmol of the total organolithium compound added.

The polar additive may be at least one selected from the group consisting of tetrahydrofuran, ditetrahydrofurylpropane, diethyl ether, cycloamyl ether, dipropyl ether, ethylene dimethyl ether, diethylene glycol, dimethyl ether, tertiary butoxyethoxyethane bis(3-dimethylaminoethyl) ether, (dimethylaminoethyl) ethyl ether, trimethylamine, triethylamine, tripropylamine, and tetramethylethylenediamine.

In the preparation method according to an embodiment of the present invention, when conjugated diene-based monomers and aromatic vinyl-based monomers are copolymerized with the addition of the polar additive, the difference of the reaction rates between them may be compensated and a random copolymer may be easily formed.

The polymerization in the step of polymerizing may be, for example, an anion polymerization, and particularly, may be a living anionic polymerization in which an active terminal may be obtained through a propagation reaction by anions.

In addition, the polymerization may be, for example, polymerization with heating or polymerization at a constant temperature.

The polymerization with heating means a polymerization method including a step of increasing a reaction temperature by optionally applying heat after adding an organolithium compound, and the polymerization at a constant temperature means a polymerization method optionally not applying heat after adding an organolithium compound.

The polymerization temperature during the polymerization may be, for example, from −20° C. to 200° C., from 0° C. to 150° C., or from 10° C. to 120° C.

Also, there is provided in the present invention, a rubber composition including the modified conjugated diene-based polymer.

The rubber composition according to an embodiment of the present invention is characterized in including 100 parts by weight of the modified conjugated diene-based polymer; and from 0.1 parts by weight to 150 parts by weight of a filler.

In particular, the rubber composition may include the filler in an amount of 10 parts by weight to 150 parts by weight, or 50 parts by weight to 100 parts by weight.

In addition, the rubber composition may further include another rubber component in addition to the modified conjugated diene-based polymer as needed, and in this case, the rubber component may be included in an amount of 90 wt % or less on the basis of the total amount of the rubber composition. More particularly, the rubber component may be included in an amount of 1 part by weight to 900 parts by weight on the basis of 100 parts by weight of the modified conjugated diene-based copolymer.

The rubber component may be a natural rubber or a synthetic rubber, and the rubber component may be, for example, a natural rubber (NR) including cis-1,4-polyisoprene; a modified natural rubber which is obtained by modifying or purifying a common natural rubber, such as an epoxidized natural rubber (ENR), a deproteinized natural rubber (DPNR), and a hydrogenated natural rubber; and a synthetic rubber such as a styrene-butadiene copolymer (SBR), polybutadiene (BR), polyisoprene (IR), a butyl rubber (IIR), an ethylene-propylene copolymer, polyisobutylene-co-isoprene, neoprene, poly(ethylene-co-propylene), poly(styrene-co-butadiene), poly(styrene-co-isoprene), poly(styrene-co-isoprene-co-butadiene), poly(isoprene-co-butadiene), poly(ethylene-co-propylene-co-diene), a polysulfide rubber, an acryl rubber, a urethane rubber, a silicone rubber, an ethylene chlorohydrin rubber, a butyl rubber, a halogenated butyl rubber, and one or a mixture of at least two thereof may be used.

The filler may be at least one selected from the group consisting of a silica-based filler, carbon black, and a mixture thereof. In the case where the filler is a silica-based filler, dispersibility may be largely improved, and hysteresis loss may be largely decreased due to the combination of silica particles with the terminal of the modified conjugated diene-based polymer of the present invention.

Meanwhile, in the case where the silica-based filler is used as the filler, a silane coupling agent may be used together for the improvement of reinforcing and low exothermic properties.

The silane coupling agent may particularly include bis(3-triethoxysilylpropyl)tetrasulfide, bis(3-triethoxysilylpropyl)trisulfide, bis(3-triethoxysilylpropyl)disulfide, bis(2-triethoxysilylethyl)tetrasulfide, bis(3-trimethoxysilylpropyl)tetrasulfide, bis(2-trimethoxysilylethyl)tetrasulfide, 3-mercaptopropyltrimethoxysilane, 3-mercaptopropyltriethoxysilane, 2-mercaptoethyltrimethoxysilane, 2-mercaptoethyltriethoxysilane, 3-trimethoxysilylpropyl-N,N-dimethylthiocarbamoyltetrasulfide, 3-triethoxysilylpropyl-N,N-dimethylthiocarbamoyltetrasulfide, 2-triethoxysilylethyl-N,N-dimethylthiocarbamoyltetrasulfide, 3-trimethoxysilylpropylbenzothiazolyltetrasulfide, 3-triethoxysilylpropylbenzolyltetrasulfide, 3-triethoxysilylpropylmethacrylatemonosulfide, 3-trimethoxysilylpropylmethacrylatemonosulfide, bis(3-diethoxymethylsilylpropyl)

tetrasulfide, 3-mercaptopropyldimethoxymethylsilane, dimethoxymethylsilylpropyl-N,N-dimethylthiocarbamoyltetrasulfide, or dimethoxymethylsilylpropylbenzothiazolyltetrasulfide, and one or a mixture of at least two thereof may be used. More particularly, the silane coupling agent may be the bis(3-triethoxysilylpropyl)polysulfide or the 3-trimethoxysilylpropylbenzothiazyltetrasulfide in consideration of the improving effect of reinforcing properties.

In addition, in the rubber composition according to an embodiment of the present invention, a modified conjugated diene-based polymer, in which a functional group having high affinity with a silica-based filler is introduced to an active portion as a rubber component, is used, and the amount of mixing of the silane coupling agent may be smaller than a common case. In particular, the silane coupling agent may be used in an amount of 1 part by weight to 20 parts by weight on the basis of 100 parts by weight of the silica-based filler. When used in the above range, effects as a coupling agent may be sufficiently exhibited, and the gelation of the rubber component may be prevented. More particularly, the silane coupling agent may be used in an amount of 5 parts by weight to 15 parts by weight on the basis of 100 parts by weight of silica.

In addition, the rubber composition according to an embodiment of the present invention may be sulfur crosslinkable, and so may further include a vulcanizing agent.

The vulcanizing agent may be particularly a sulfur powder and may be included in an amount of 0.1 parts by weight to 10 parts by weight on the basis of 100 parts by weight of a rubber component. With the amount of the vulcanizing agent in the above range, elasticity and strength required for a vulcanized rubber composition may be secured, and at the same time, a low combustion ratio may be attained.

In addition, the rubber composition according to an embodiment of the present invention may further include various additives used in a common rubber industry in addition to the above components, particularly, a vulcanization accelerator, a process oil, a plasticizer, an antiaging agent, a scorch preventing agent, a zinc white, stearic acid, a thermosetting resin, or a thermoplastic resin.

The vulcanization accelerator is not specifically limited and may particularly include a thiazole-based compound such as 2-mercaptobenzothiazole (M), dibenzothiazyldisulfide (DM), and N-cyclohexyl-2-benzothiazylsulfenamide (CZ), or a guanidine-based compound such as diphenylguanidine (DPG). The vulcanization accelerator may be included in an amount of 0.1 parts by weight to 5 parts by weight on the basis of 100 parts by weight of the rubber component.

In addition, the process oil acts as a softener in a rubber composition and may particularly include paraffin-based, naphthene-based, or aromatic compounds. More particularly, an aromatic process oil may be used in consideration of tensile strength and abrasion resistance, and the naphthene-based or paraffin-based process oil may be used in consideration of hysteresis loss and low temperature properties. The process oil may be included in an amount of 100 parts by weight or less on the basis of 100 parts by weight of the rubber component. When the process oil is included in the above-described amount, the deterioration of the tensile strength and the low exothermic properties (low fuel combustion ratio) of the vulcanized rubber may be prevented.

In addition, the antiaging agent may particularly include N-isopropyl-N'-phenyl-p-phenylenediamine, N-(1,3-dimethylbutyl)-N'-phenyl-p-phenylenediamine, 6-ethoxy-2,2,4-trimethyl-1,2-dihydroquinoline, or a condensate of diphenylamine and acetone at a high temperature. The antiaging agent may be used in an amount of 0.1 parts by weight to 6 parts by weight on the basis of 100 parts by weight of the rubber component.

The rubber composition according to an embodiment of the present invention may be obtained by mulling using a mulling apparatus such as a banbury mixer, a roll, and an internal mixer according to a mixing prescription. In addition, a rubber composition having low exothermic properties and good abrasion resistance may be obtained due to a vulcanization process after a molding process.

Therefore, the rubber composition may be usefully used for the manufacture of each member of a tire such as a tire tread, an under tread, a side wall, a carcass coating rubber, a belt coating rubber, a bead filler, a chafer, and a bead coating rubber, or for the manufacture of rubber products for various industries such as a dustproof rubber, a belt conveyor, and a hose.

Also, there is provided in the present invention a tire manufactured using the rubber composition.

The tire may include a tire or a tire tread.

The present invention relates to a tire or a tire tread including the modified conjugated diene-based polymer rubber composition.

The tire or the tire tread may be manufactured using the rubber composition, and has merits of excellent tensile strength, abrasion resistance, and wet traction, and low rolling resistance.

Hereinafter, the present invention will be explained in particular referring to non-limiting embodiments. It will be understood that words or terms used in the specification and claims shall not be interpreted as the meaning defined in commonly used dictionaries. It will be further understood that the words or terms should be interpreted as having a meaning that is consistent with the technical idea of the invention, based on the principle that an inventor may properly define the meaning of the words or terms to best explain the invention.

Accordingly, the following embodiments are merely presented to exemplify the present invention, and various modifications and changes within the scope and technical spirit of the present invention would be obvious to a person skilled in the art, and such modifications and changes are definitely included in attached claims.

Preparation Example

In a flask, 60 g of cyclohexane was allowed to react with N,N'-dimethylpropane-1,3-diamine (2.04 g, 0.02 mol) and 1-bromo-3-chloropropane (6.93 g, 0.044 mol), and stirring at 60° C. for 4 hours was conducted. Li (1.39 g, 0.2 mol) was added to the solution thus obtained, followed by stirring at 40° C. for 12 hours, and then, an unreacted material was removed, isoprene (2.72 g, 0.04 mol) was added thereto, and stirring was conducted at 40° C. for 1 hour to prepare an organolithium compound represented by Formula 2 below. In the organolithium compound thus prepared and represented by Formula 2, active Li concentration was measured via a titration method using diphenyl acetic acid, and the active Li concentration thus measured was 0.55 M (83% degree in comparison with a calculated active Li concentration (0.66 M)).

[Formula 2]

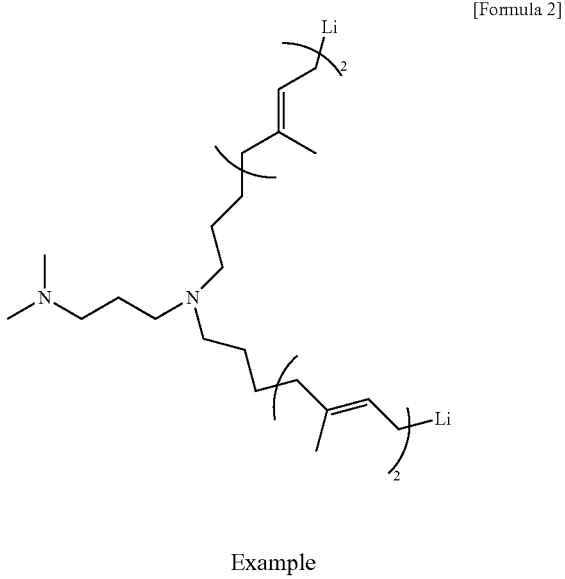

Example

To a 20 L autoclave reactor, 270 g of styrene, 710 g of 1,3-butadiene, 5,000 g of normal hexane, and 1.3 g of 2,2-bis(2-oxoranyl)propane as a polar additive were added, and the internal temperature of the reactor was elevated to 40° C. When the temperature in the reactor reached 40° C., 0.4 mmol of the organolithium compound of Formula 2 prepared in the preparation example was injected into the reactor, and an adiabatic reaction with heating was performed. After about 20 minutes, 20 g of 1,3-butadiene was added, after 5 minutes, 0.7 g of bis(3-triethoxymethylsilyl-propyl)-N-methylamine was injected, and the reaction was continued for 15 minutes. After that, a polymerization reaction was quenched using ethanol, and 5 ml of a solution of 0.3 wt % of butylated hydroxytoluene (BHT) as an antioxidant dissolved in hexane was added thereto. The polymer thus obtained was injected to hot water heated with steam, stirred to remove solvents, and roll dried to remove remaining solvents and water to prepare a modified styrene-butadiene copolymer.

Comparative Example

A styrene-butadiene copolymer was prepared by the same method described in Example except for using 0.4 mmol of n-butyllithium instead of the organolithium compound represented by Formula 2 as a polymerization initiator.

Experimental Example 1

With respect to each of the modified styrene-butadiene copolymer of Example and the styrene-butadiene copolymer of Comparative Example, molecular weight analysis, component analysis, and mooney viscosity (MU) measurement were conducted. The results are listed in Table 1 below.

1) Mooney Viscosity

Two specimens having a weight of at least 15 g were pre-heated for 1 minute and then heated at 100° C. for 4 minutes, and measurement was conducted using MV-2000 manufactured by ALPHA Technologies Co., Ltd.

2) Component Analysis

The styrene derived unit (SM) content and the vinyl content in each copolymer were measured by using NMR.

3) Molecular Weight Analysis

The maximum peak molecular weight (Mp), weight average molecular weight (Mw), and number average molecular weight (Mn) of each copolymer were measured by gel permeation chromatography (GPC) analysis under conditions of 40° C. In this case, two columns of PLgel Olexis and one column of PLgel mixed-C manufactured by Polymer Laboratories Co. Ltd. were used in combination as columns, and all newly replaced columns were mixed bed type columns. In addition, polystyrene (PS) was used as a GPC standard material for calculating the molecular weight. Polydispersity index (PDI) was calculated as a ratio (Mw/Mn) of the weight average molecular weight and the number average molecular weight, which were measured by the above method.

TABLE 1

| Division | | Example | Comparative Example |
|---|---|---|---|
| Mooney viscosity (MV) | | 88 | 77 |
| NMR | Styrene | 27 | 27 |
| | Vinyl | 42 | 43 |
| GPC ($\times 10^4$) | Mp | 28.2 | 24.9 |
| | Mn | 25.3 | 24.0 |
| | Mw | 29.1 | 25.7 |
| | PDI | 1.15 | 1.07 |

Experimental Example 2

In order to comparatively analyze the physical properties of a rubber composition including each copolymer of Example and Comparative Example and tires manufactured from the rubber compositions, tensile properties and viscoelasticity properties were measured. The results are listed in Table 2 below.

1) Preparation of Rubber Composition

Each rubber composition was prepared via a first stage mulling and a second stage mulling. In this case, the amounts used of materials except for a modified styrene-butadiene copolymer were indicated on the basis of 100 parts by weight of the copolymer. In the first stage mulling, 100 parts by weight of each copolymer, 70 parts by weight of silica, 11.1 parts by weight of bis(3-triethoxysilylpropyl) tetrasulfide as a silane coupling agent, 2 parts by weight of an antiaging agent (TMDQ), 2 parts by weight of an antioxidant, 3 parts by weight of zinc oxide (ZnO), 2 parts by weight of stearic acid, and 1 part by weight of wax were mixed and mulled at 80 rpm conditions by using a banbury mixer equipped with a temperature controlling apparatus. In this case, the temperature of the mulling apparatus was controlled, and a first mixture was obtained at a discharge temperature of 145° C. to 150° C. At the second stage mulling, the first mixture was cooled to room temperature, and 1.75 parts by weight of a rubber accelerator (CZ), 1.5 parts by weight of a sulfur powder, and 2 parts by weight of a vulcanization accelerator were added to the mulling apparatus and mixed at a temperature of 100° C. or less to obtain a second mixture. Then, each vulcanized rubber was prepared by vulcanizing using a vulcanizing press at 180° C. for t90+10 minutes.

2) Tensile Properties

Tensile properties were measured by manufacturing a specimen (thickness 25 mm, length 80 mm) and measuring tensile strength when breaking and tensile stress when elongated by 300% (300% modulus) of each specimen according to an ASTM 412 tension test method. Particularly, a Universal Test machine 4204 tension tester of Instron Co., Ltd. was used, and measurement was performed at room temperature at a rate of 50 cm/min, to obtain a tensile strength value and a tensile stress value when elongated by 300%.

3) Viscoelasticity Properties

Viscoelasticity properties were measured by using a dynamic mechanical analyzer of TA Co., Ltd. A Tan δ value was measured by changing deformation at each measurement temperature (−60° C. to 60° C.) with a twist mode and a frequency of 10 Hz. If the Tan δ value at a low temperature of 0° C. increases, wet traction becomes good, and if the Tan δ value at a high temperature of 60° C. decreases, hysteresis loss decreases, low rolling resistance of a tire, i.e., a low fuel consumption ratio becomes good.

TABLE 2

| Specimen | Example | Comparative Example |
|---|---|---|
| 300% modulus (Kgf/cm$^2$) | 132 | 130 |
| Tensile strength (Kgf/cm$^2$) | 201 | 197 |
| Tan at 0° C. | 0.967 | 0.922 |
| Tan at 60° C. | 0.101 | 0.120 |

As shown in Table 2, the tensile and viscoelasticity properties of the rubber composition including the modified styrene-butadiene copolymer according to Example, which was prepared using the organolithium compound according to an embodiment of the present invention as a polymerization initiator, were secured to be better when compared to those of the rubber composition including the styrene-butadiene copolymer of Comparative Example.

In particular, when compared to the rubber composition including the styrene-butadiene copolymer of Comparative Example, it was secured that a Tan δ value at 0° C. was increased, and a Tan δ value at 60° C. was decreased for the rubber composition including the modified styrene-butadiene copolymer according to Example, which was prepared using the organolithium compound according to an embodiment of the present invention as a polymerization initiator. The results indicate that the modified styrene-butadiene copolymer prepared using the organolithium compound according to an embodiment of the present invention as a polymerization initiator attained good wet traction and rolling resistance, and a high fuel consumption ratio.

The invention claimed is:

1. An organolithium compound represented by the following Formula 1:

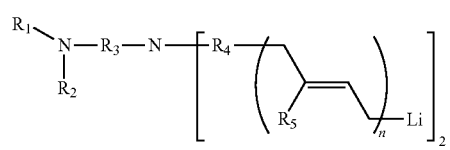

[Formula 1]

in Formula 1, $R_1$, $R_2$ and $R_5$ are each independently a monovalent hydrocarbon group having 1 to 10 carbon atoms, $R_3$ and $R_4$ are each independently a divalent hydrocarbon group having 1 to 10 carbon atoms, and n is an integer of 1 to 5.

2. The organolithium compound of claim 1, wherein in Formula 1, $R_1$, $R_2$ and $R_5$ are each independently an alkyl group having 1 to 6 carbon atoms, $R_3$ and $R_4$ are each independently an alkylene group having 1 to 6 carbon atoms, and n is an integer of 1 to 3.

3. The organolithium compound of claim 1, wherein the organolithium compound represented by Formula 1 is represented by the following Formula 2:

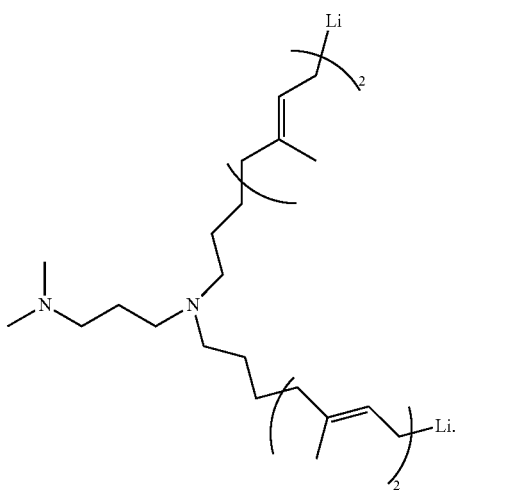

[Formula 2]

4. The organolithium compound of claim 1, wherein the organolithium compound is a polymerization initiator for a polymer containing conjugated diene-based monomer-derived units.

5. A method for preparing a modified conjugated diene-based polymer represented by the following Formula 3:

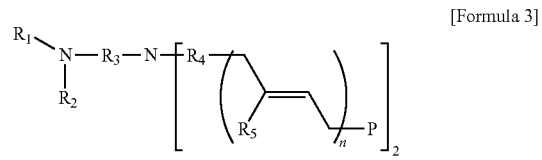

[Formula 3]

in Formula 3,
$R_1$, $R_2$ and $R_5$ are each independently a monovalent hydrocarbon group having 1 to 10 carbon atoms,
$R_3$ and $R_4$ are each independently a divalent hydrocarbon group having 1 to 10 carbon atoms,
n is an integer of 1 to 5, and
P is a conjugated diene-based polymer chain, the method comprising:
polymerizing conjugated diene-based monomers, or conjugated diene-based monomers and aromatic vinyl-based monomers in the presence of an organolithium compound represented by the following Formula 1 in a hydrocarbon solvent:

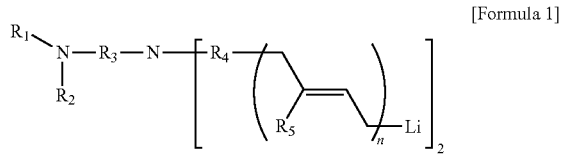

[Formula 1]

in Formula 1,
$R_1$, $R_2$ and $R_5$ are each independently a monovalent hydrocarbon group having 1 to 10 carbon atoms, R$_3$ and R$_4$ are each independently a divalent hydrocarbon group having 1 to 10 carbon atoms, and n is an integer of 1 to 5

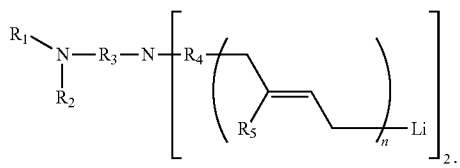

6. The method for preparing the modified conjugated diene-based polymer of claim 5, wherein the organolithium compound represented by Formula 1 is represented by the following Formula 2:

[Formula 2]

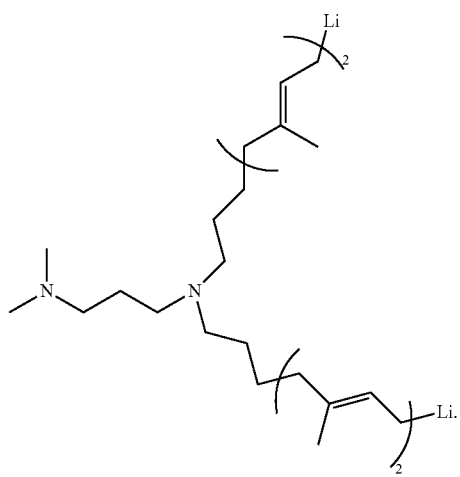

7. The method for preparing the modified conjugated diene-based polymer of claim 5, wherein the organolithium compound is used from 0.01 mmol to 10 mmol on the basis of 100 g of total monomers.

8. The method for preparing the modified conjugated diene-based polymer of claim 5, wherein the conjugated diene-based monomer is at least one selected from the group consisting of 1,3-butadiene, 2,3-dimethyl-1,3-butadiene, piperylene, 3-butyl-1,3-octadiene, isoprene, and 2-phenyl-1,3-butadiene.

9. The method for preparing the modified conjugated diene-based polymer of claim 5, wherein the aromatic vinyl-based monomer is at least one selected from the group consisting of styrene, a-methylstyrene, 3-methylstyrene, 4-methylstyrene, 4-propylstyrene, 1-vinylnaphthalene, 4-cyclohexylstyrene, 4-(p-methylphenyl)styrene, and 1-vinyl-5-hexylnaphthalene.

10. The method for preparing the modified conjugated diene-based polymer of claim 5, wherein the polymerizing is performed using a polar additive.

11. The method for preparing the modified conjugated diene-based polymer of claim 10, wherein the polar additive is added from 0.001 g to 10 g on the basis of 1 mmol of the organolithium compound in total.

12. The method for preparing the modified conjugated diene-based polymer of claim 10, wherein the polar additive is at least one selected from the group consisting of tetrahydrofuran, ditetrahydrofurylpropane, diethyl ether, cycloamyl ether, dipropyl ether, ethylene dimethyl ether, diethylene glycol, dimethyl ether, tertiary butoxyethoxyethane bis(2-dimethylaminoethyl)ether, (dimethylaminoethyl)ethyl ether, trimethylamine, triethylamine, tripropylamine, and tetramethylethylenediamine.

* * * * *